United States Patent
Chiou et al.

(10) Patent No.: US 9,964,521 B2
(45) Date of Patent: May 8, 2018

(54) DETECTING DAMAGE IN A COMPOSITE PANEL WITHOUT REMOVING OVERLYING INSULATION

(71) Applicant: ROHR, INC., Chula Vista, CA (US)

(72) Inventors: Song Chiou, Irvine, CA (US); Jared Victor, San Diego, CA (US); Vijay V. Pujar, San Diego, CA (US)

(73) Assignee: ROHR, INC., Chula Vista, CA (US)

( * ) Notice: Subject to any disclaimer, the term of this patent is extended or adjusted under 35 U.S.C. 154(b) by 252 days.

(21) Appl. No.: 14/553,229

(22) Filed: Nov. 25, 2014

(65) Prior Publication Data

US 2016/0313286 A1    Oct. 27, 2016

(51) Int. Cl.
| | | |
|---|---|---|
| *G01N 29/04* | (2006.01) | |
| *B64D 27/10* | (2006.01) | |
| *B64D 29/00* | (2006.01) | |
| *G01M 15/14* | (2006.01) | |

(52) U.S. Cl.
CPC ............ *G01N 29/043* (2013.01); *B64D 27/10* (2013.01); *B64D 29/00* (2013.01); *G01M 15/14* (2013.01); *G01N 2291/0231* (2013.01); *G01N 2291/0289* (2013.01); *G01N 2291/102* (2013.01); *G01N 2291/2693* (2013.01)

(58) Field of Classification Search
CPC ......... G01N 29/043; G01N 2291/0231; G01N 2291/0289; G01N 2291/102; B64D 27/10; B64D 29/00; G01M 15/14
USPC .......................................................... 73/644
See application file for complete search history.

(56) References Cited

U.S. PATENT DOCUMENTS

| | | | | | |
|---|---|---|---|---|---|
| 4,783,997 | A  * | 11/1988 | Lynnworth | ............... | B06B 3/00 |
| | | | | | 73/644 |
| 4,976,150 | A  * | 12/1990 | Deka | .................. | G01N 29/2437 |
| | | | | | 73/644 |
| 7,721,606 | B2 * | 5/2010 | Shirai | .................. | G01N 29/043 |
| | | | | | 73/597 |
| 8,047,081 | B2 * | 11/2011 | Berberig | ................. | G01F 1/662 |
| | | | | | 73/644 |
| 2007/0266789 | A1* | 11/2007 | Hampton | ............... | G01N 29/11 |
| | | | | | 73/596 |

OTHER PUBLICATIONS

Humeida et al., A Probabilistic Approach for the Optimisation of Ultrasonic Array Inspection Techniques, NDT & E International, vol. 68, Dec. 2014, pp. 43-52.

* cited by examiner

Primary Examiner — Lisa Caputo
Assistant Examiner — Tarun Sinha
(74) Attorney, Agent, or Firm — Snell & Wilmer, L.L.P.

(57) ABSTRACT

Systems and methods for detecting damage in composite components are disclosed. A first attachment feature and a second attachment feature may be coupled to a composite component. A transmitting device may be coupled to the first attachment feature. A receiving device may be coupled to the second attachment feature. A signal may be transmitted from the transmitting device, through the first attachment feature, through the composite component, and through the second attachment feature to the receiving device. The signal may be analyzed to detect damage in the composite component.

11 Claims, 5 Drawing Sheets

DETECTING DAMAGE IN A COMPOSITE PANEL WITHOUT REMOVING OVERLYING INSULATION

FIELD

The present disclosure relates to turbine engine systems and, more specifically, to detecting damage in composite components in turbine engines.

BACKGROUND

Aircraft nacelle structures for turbine engines typically include composite structures which provide significant weight advantages to heavier metal materials. The composite structures may comprise, for example, a composite back skin and a composite top skin with a core material sandwiched in between. A thermal protection system may be coupled to the composite back skin via a plurality of attachment features. The thermal protection system may insulate the composite back skin from high temperatures in the engine, and may provide protection to the composite structure from thermal damage, such as delamination of the composite structure. However, the thermal protection system may obscure direct access to the composite back skin and make it difficult to detect damage in the composite back skin using conventional inspection techniques. Typically, the thermal protection system needs to be removed in order to inspect the composite back skin for any thermal or structural damage. However, removing and reinstalling the thermal protection system is time consuming and may result in damage to the thermal protection system or the composite structures. There is a need for methods to inspect the structural integrity of composite structures configured with thermal protection blankets without having to remove the thermal protection blankets or without direct access to the composite structure, and for methods that more objectively detect and measure damage through means other than direct contact with a composite structure.

SUMMARY

A method of detecting damage in a composite component may comprise coupling a transmitting device to a first attachment feature. The first attachment feature may be coupled to the composite component, and the first attachment feature may be configured to couple a thermal protection system to the composite component. A receiving device may be coupled to a second attachment feature. The second attachment feature may be coupled to the composite component, and the second attachment feature may be configured to couple the thermal protection system to the composite component. An ultrasonic wave may be generated by the transmitting device. The receiving device may receive the ultrasonic wave.

A method for detecting damage in a composite component may comprise coupling a transmitting device to a first attachment feature. A receiving device may be coupled to a second attachment feature. The transmitting device may transmit a signal through the first attachment feature, through a composite component, and through the second attachment feature to the receiving device.

A method of detecting damage in a composite structure may comprise transmitting an ultrasonic wave form through a first device for coupling an insulation layer to a composite component. The ultrasonic wave form may be received through a second device for coupling the insulation layer to the composite structure. The ultrasonic wave form may be compared to an expected wave form for an undamaged composite structure.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing figures, wherein like numerals denote like elements.

DETAILED DESCRIPTION

The detailed description of various embodiments herein makes reference to the accompanying drawings, which show various embodiments by way of illustration. While these various embodiments are described in sufficient detail to enable those skilled in the art to practice the inventions, it should be understood that other embodiments may be realized and that logical, chemical and mechanical changes may be made without departing from the spirit and scope of the inventions. Thus, the detailed description herein is presented for purposes of illustration only and not of limitation. For example, the steps recited in any of the method or process descriptions may be executed in any order and are not necessarily limited to the order presented.

Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

A nacelle structure may comprise a composite component. The composite component may be a honeycomb core sandwiched between a composite top skin and composite back skin layer. One of the composite skin layers may be perforated to form an acoustic structure that provides noise reduction. A thermal protection system, such as an insulation blanket, may be coupled to the composite component to protect the composite component from high temperatures. A plurality of attachment features may be coupled to the composite component in order to secure the thermal protection system to the composite component. The attachment features may extend through the thermal protection system. A transmitting device may be coupled to a first attachment feature, and a receiving device may be coupled to the second attachment feature. The transmitting device may transmit a signal, such as an ultrasonic wave or array, through the first attachment feature, through the composite component, and through the second attachment feature to the receiving device. The receiving device may receive the signal. The signal may be used and analyzed to identify damage in the composite component. Thus, damage may be detected in the composite component without removing the thermal protection system.

Figure 1:
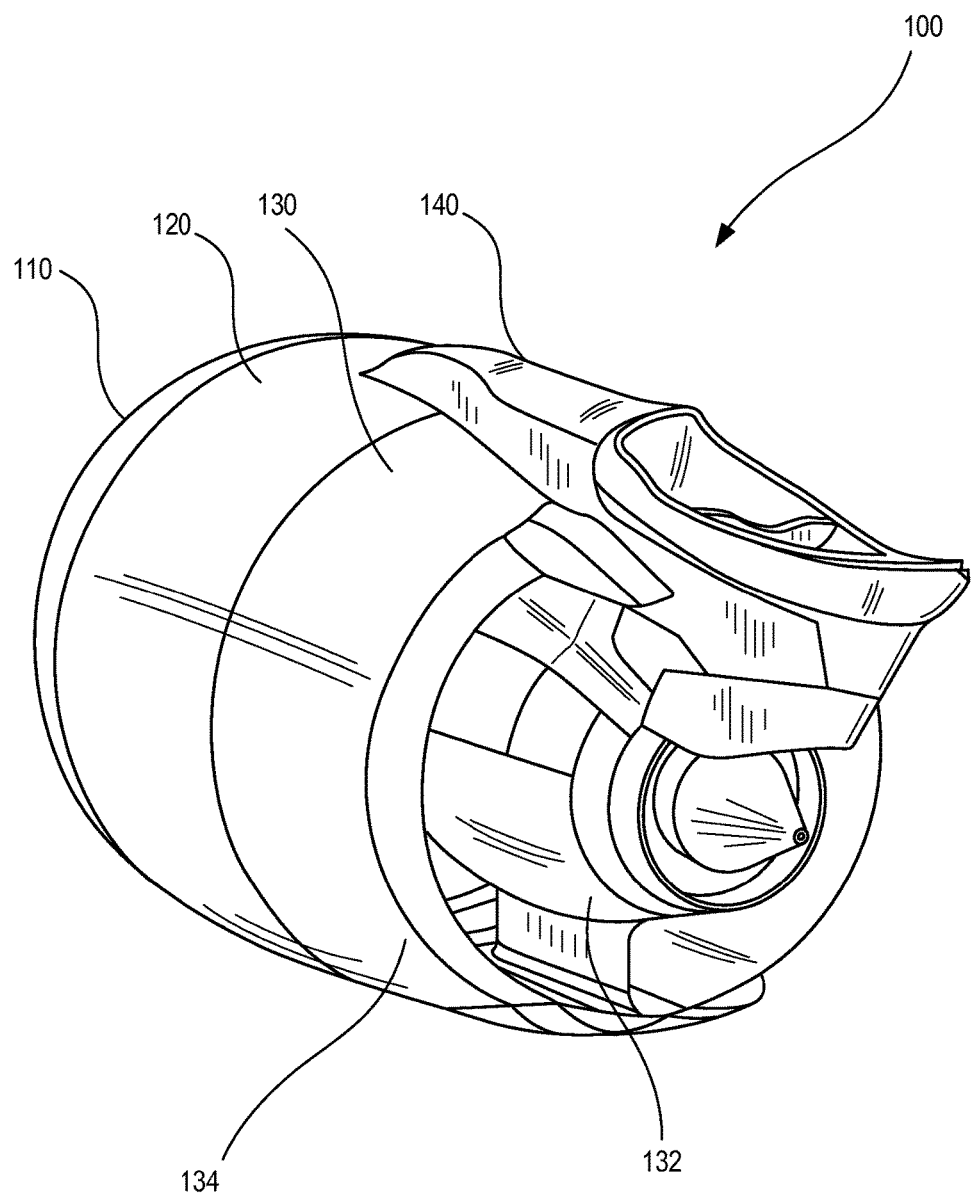
FIG. 1 illustrates a perspective view of a nacelle in accordance with various embodiments.

Referring to FIG. 1, a nacelle 100 for a gas turbine engine is illustrated according to various embodiments. Nacelle 100 may comprise an inlet 110, a fan cowl 120, and a thrust reverser 130. Nacelle 100 may be coupled to a pylon 140, which may mount the nacelle 100 to an aircraft wing or aircraft body. Thrust reverser 130 may comprise an inner fixed structure ("IFS") 132 and a translating sleeve 134. Bypass air from an engine fan may flow between the IFS 132 and the translating sleeve 134. The nacelle 100 may comprise composite components, such as within the IFS 132, which are subjected to high temperatures. Thermal protection systems may be coupled to the composite components to protect the composite components from the high temperatures.

Figure 2A:
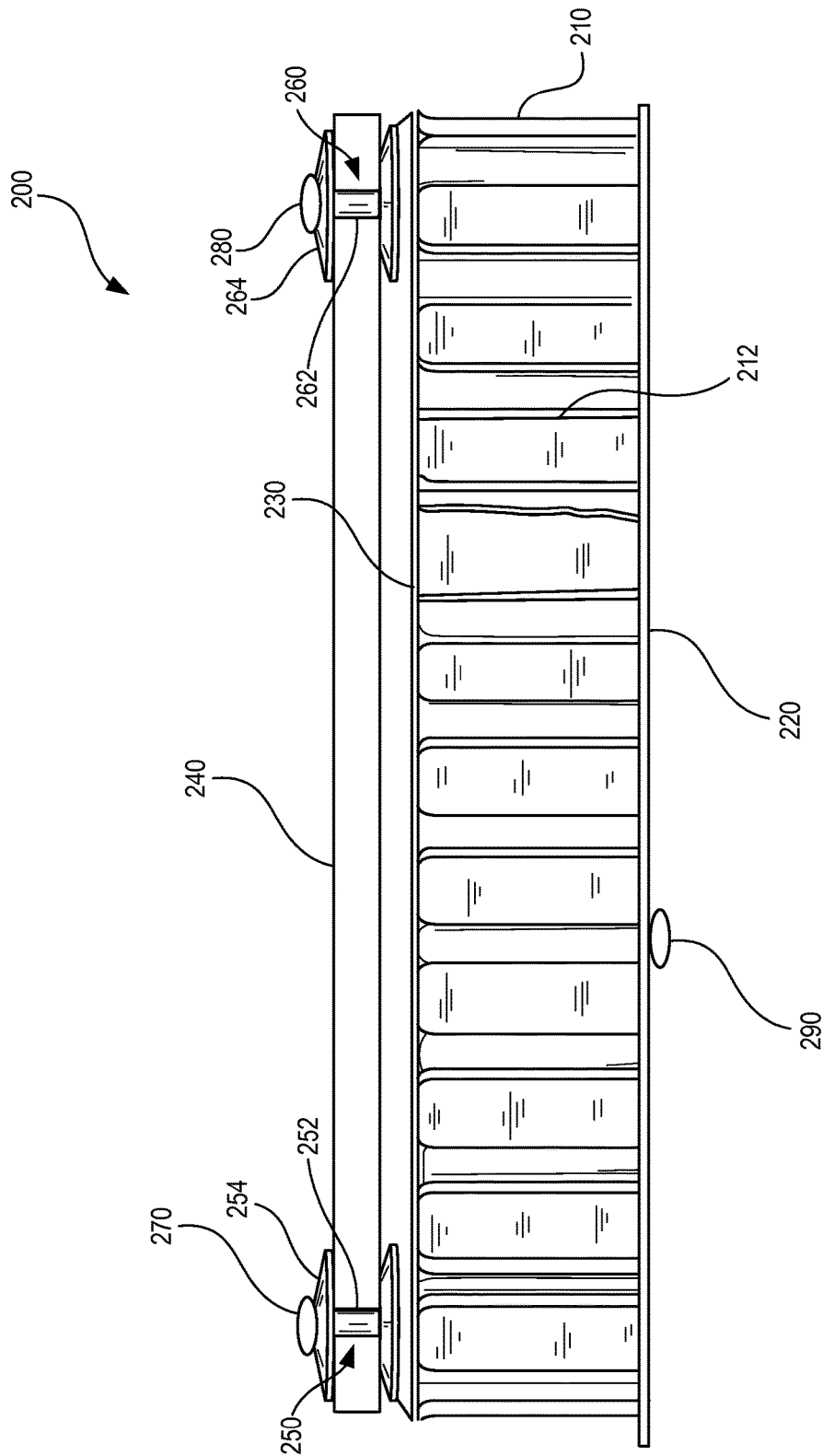
FIG. 2A illustrates a schematic view of a composite structure in accordance with various embodiments.

Referring to FIG. 2A, a composite structure 200 is illustrated according to various embodiments. The acoustic structure may comprise a core 210, positioned between an optionally perforated top sheet 220 and a back skin 230. The core 210 may comprise a plurality of honeycomb cells 212. One side of the composite structure 200 may be closed by a generally rigid back skin 230. In various embodiments, the back skin 230 may be non-perforated. A top sheet 220 having perforations may be coupled to the composite structure 200 opposite the back skin 230. The top sheet 220, core 210, and back skin 230 combine to form honeycomb cells 212 that become resonating chambers and work to cancel the sound waves from an aircraft engine and help to reduce the noise from the engine.

In various embodiments, at least one of the back skin 230 or the top sheet 220 may comprise a composite material. The composite material may comprise a plurality of composite plies assembled in a composite laminate. Each composite ply may comprise high-strength carbon fiber reinforcements in a toughened epoxy polymer matrix. However, many other types of fibers, such as glass, aramid, polyethylene, boron, and silicon carbide may be used in many other types of matrix materials, including without limitation, thermosetting resins, thermoplastics, and ceramics. A thermal protection system 240 may be coupled to the back skin 230 to protect the back skin 230 and the rest of the composite structure from high temperatures. The thermal protection system 240 may comprise a low density insulating material. A first attachment feature 250 and a second attachment feature 260 may be coupled to the back skin 230. Any number of attachment features may be coupled to the back skin 230. In various embodiments, the attachment features may be a disk and post fastener, such as a CLICK BOND® attachment feature manufactured by Click Bond, Inc. In various embodiments, the first attachment feature 250 and the second attachment feature 260 may comprise metal. The first attachment feature 250 and the second attachment feature 260 may be capable of transmitting and/or receiving ultrasonic signals, such as ultrasonic waves, without significant signal loss. In various embodiments, the first attachment feature 250 and the second attachment feature 260 may be coupled to the back skin 230 with an adhesive. The first attachment feature 250 and the second attachment feature 260 may extend through apertures in the thermal protection system 240 in order to retain the thermal protection system 240 adjacent to the back skin 230. The first attachment feature 250 and the second attachment feature 260 may each comprise a post 252, 262, and a cap 254, 264, respectively. The caps 254, 264 may be removably coupled to the posts 252, 262. For example, the caps 254, 264, may threadingly engage the posts 252, 262. The caps 254, 264, may be separated from the posts 252, 262 in order to remove the thermal protection system 240 and access the back skin 230. In various embodiments, the caps 254, 264 and the posts 252, 262 may be specially designed to be capable of transmitting and/or receiving ultrasonic signals, such as ultrasonic waves, without significant signal loss.

A transmitting device 270 may be coupled to the first attachment feature 250. The transmitting device 270 may be configured to transmit a signal, such as an ultrasonic or electromagnetic wave form or array, through the first attachment feature 250. In various embodiments, the transmitting device 270 may comprise a piezoelectric transducer. In various embodiments, the transmitting device 270 may transmit an ultrasonic wave pattern through the first attachment feature 250.

A receiving device 280 may be coupled to the second attachment feature 260. The receiving device 280 may be configured to receive a signal through the second attachment feature 260. The signal may travel from the transmitting device 270, through the first attachment feature 250, through the back skin 230, through the second attachment feature 260, and to the receiving device 280. In various embodiments, the receiving device 280 may comprise a piezoelectric transducer. In various embodiments, the receiving device 280 may receive an ultrasonic wave pattern through the second attachment feature 260. The signal received by the receiving device 280 may be compared to an expected signal which would be received through an undamaged back skin. Discrepancies between the signal received by the receiving device 280 and the expected signal may indicate damage to the back skin 230. If damage is detected to the back skin 230, the thermal protection system 240 may be inspected and/or removed in order to repair or replace the back skin 230. In various embodiments, a plurality of receiving devices 280 may be distributed on the back skin 230. The plurality of receiving devices 280 may receive the signal from the transmitting device 270, and signals received by the plurality of receiving devices 280 may be analyzed to determine a location of damage to the back skin 230.

In various embodiments, a receiving device 290 may be coupled to the top sheet 220. The transmitting device 270 may transmit a signal through the first attachment feature, through the back skin 230, through the core 210, and through the top sheet 220 to the receiving device 290. The signal may be a waveform such as an ultrasonic or electromagnetic wave. The signal may be analyzed to detect damage in the back skin 230 and/or the top sheet 220. In various embodiments, a laser may monitor vibrations in the top sheet 220. The laser may detect small displacements in the top sheet 220. The vibrations may be analyzed by comparing the observed vibrations with expected vibrations for an undamaged composite component to determine whether there is any damage to the top sheet 220 or back skin 230.

Figure 2B:
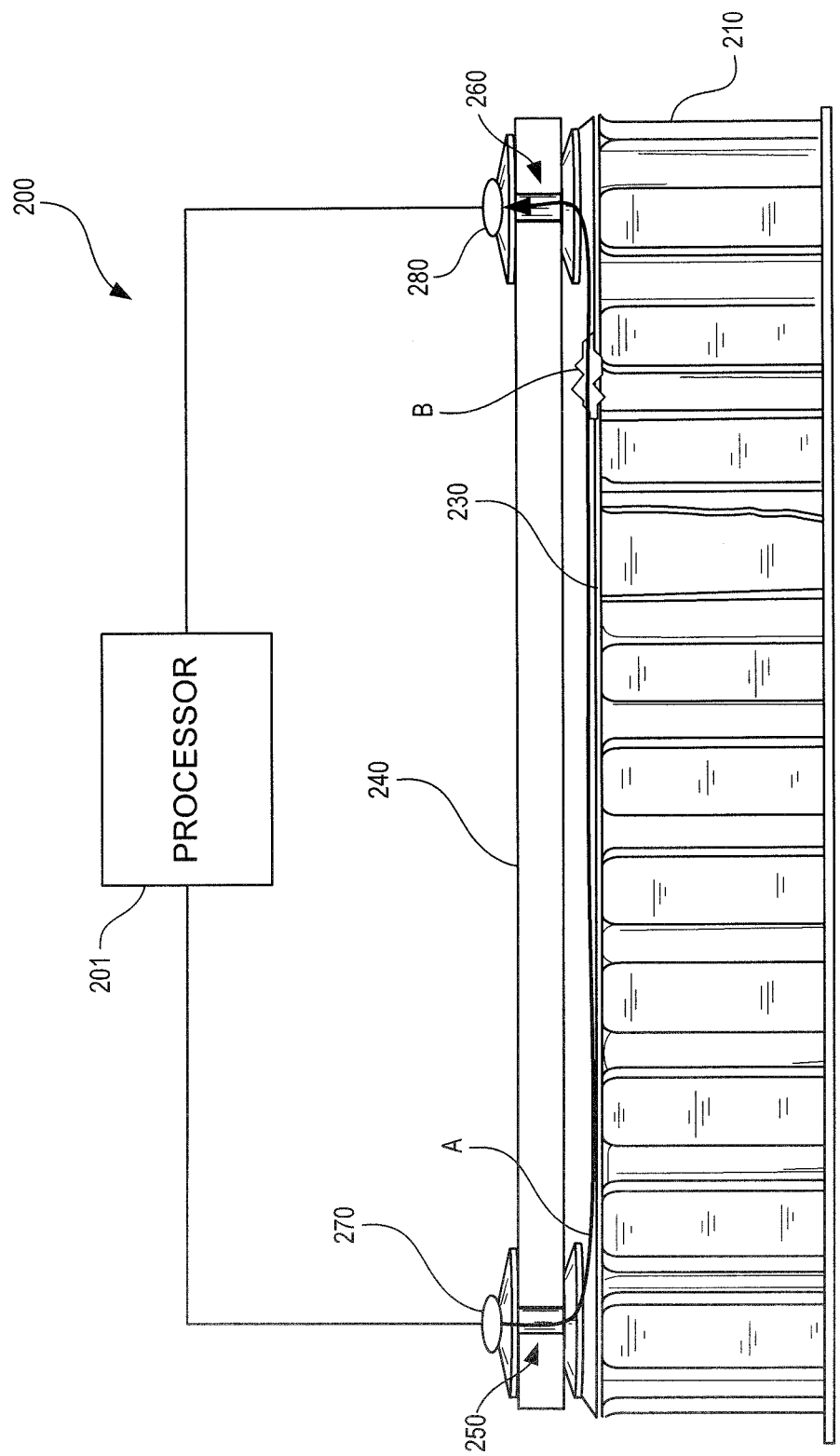
FIG. 2B illustrates a schematic view of the composite structure under test in accordance with various embodiments.

Referring to FIG. 2B, the composite structure 200 is shown being tested according to various embodiments. The acoustic structure may be tested during on-ground maintenance or inspection. A processor 201 may be electrically coupled to the transmitting device 270 and the receiving device 280. The processor 201 may transmit an electrical signal to the transmitting device 270, and the transmitting device 270 may convert the electrical signal to an ultrasonic wave form. The transmitting device 270 may transmit the ultrasonic wave form along path A through the first attachment feature 250, through the back skin 230, and through the second attachment feature 260 to the receiving device 280. The receiving device 280 may convert the received ultrasonic wave form to an electrical signal which is transmitted back to the processor 201. The processor 201 may analyze the signal received from the receiving device 280 and may detect an abnormality in the signal. For example, the ultrasonic wave form may pass through a damaged region B which may alter the ultrasonic wave form. The damaged region B may represent a delamination between the back skin 230 and the core 210, or other damage, for example, thermal degradation in the back skin 230. In response to the processor 201 detecting damage, the thermal protection system 240 may be removed in order to further inspect or replace or repair the back skin 230.

Figure 3:
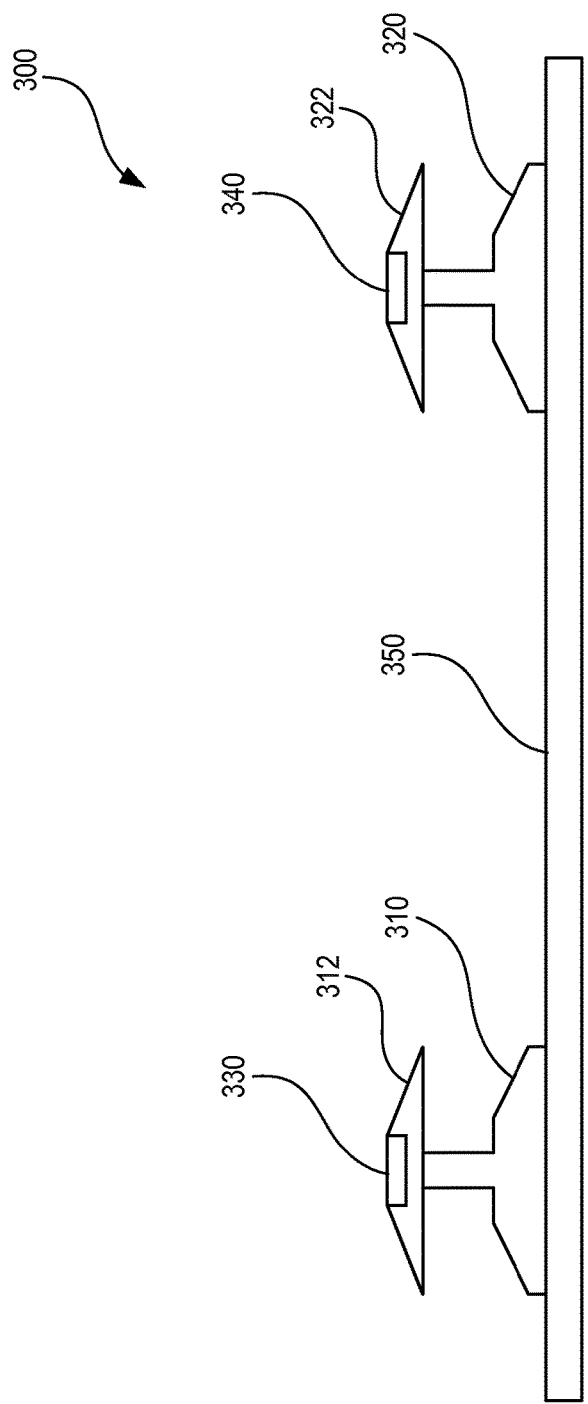
FIG. 3 illustrates a schematic view of a composite structure having embedded transmitting and receiving devices in accordance with various embodiments.

Referring to FIG. 3, a composite structure 300 comprising attachment features with embedded transducers is illustrated according to various embodiments. A first attachment feature 310 may comprise an embedded transmitting device 330, and a second attachment feature 320 may comprise an embedded receiving device 340. The transmitting device 330 may be embedded in a cap 312 of the first attachment feature 310. The receiving device 340 may be embedded in a cap 322 of the second attachment feature 320. In various embodiments, the transmitting device 330 and the receiving device 340 may be embedded in the caps 312, 322 during manufacture of the first attachment feature 310 and the second attachment feature 320. However, in various embodiments, the caps 312, 322 may be manufactured separately, and may replace existing caps. The first attachment feature 310 and the second attachment feature 320 may be coupled to a composite component 350. The composite component 350 may comprise a back skin for an acoustic structure. A signal may be transmitted from the transmitting device 330 to the receiving device 340 in order to detect damage in the composite component 350.

In various embodiments, the caps 312, 322 may be in place during normal engine operation, such as during flight as well as during maintenance. However, in various embodiments, the caps 312, 322 may temporarily replace caps without a transmitting device or receiving device during testing or maintenance in order to detect damage in the composite component 350, and the caps 312, 322 may be removed after testing and replaced by caps without a transmitting device or receiving device.

Figure 4:
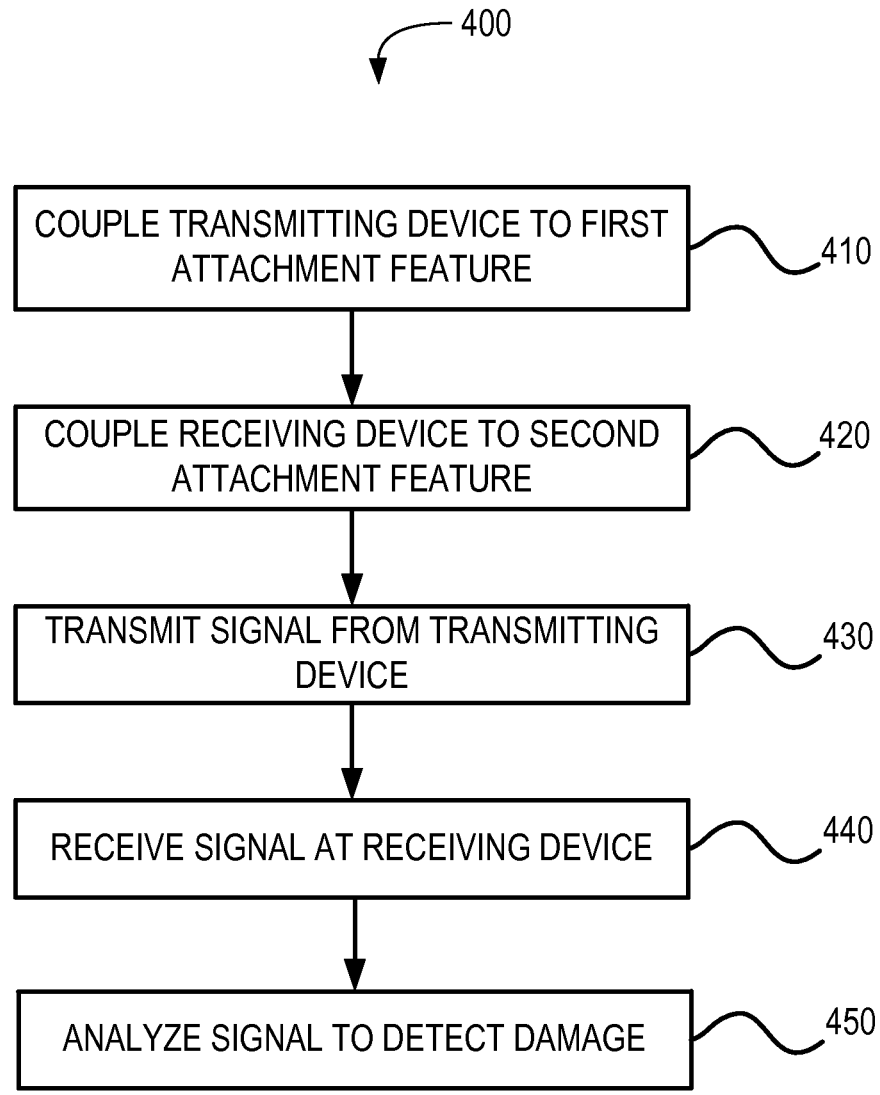
FIG. 4 illustrates a flow chart of a method for detecting damage in a composite component in accordance with various embodiments.

Referring to FIG. 4, a flowchart 400 of a process for detecting damage in a composite component is illustrated according to various embodiments. A first attachment feature and a second attachment feature may be coupled to a composite component. The first attachment feature and the second attachment feature may retain a thermal protection system adjacent to the composite component. A transmitting device may be coupled to the first attachment feature (step 410). In various embodiments, the transmitting device may be positioned in contact with the first attachment feature or temporarily adhered to the first attachment feature. However, in various embodiments, the transmitting device may be embedded within the first attachment feature. A receiving device may be coupled to the second attachment feature (step 420). In various embodiments, the receiving device may be positioned in contact with the second attachment feature or temporarily adhered to the second attachment feature. However, in various embodiments, the receiving device may be embedded within the second attachment feature. The transmitting device may transmit a signal (step 430). In various embodiments, the signal may be an ultrasonic wave pattern. The receiving device may receive the signal (step 440). The signal may travel through the first attachment feature, the composite component, and the second attachment feature. The signal may be analyzed to detect damage in the composite component (step 450). The signal received may be compared to an expected signal for a composite component without damage in order to detect any damage. For example, in various embodiments, an amplitude and signal-to noise ratio of the signal may be analyzed in order to detect a defect. An example of signal analysis for detecting damage, is described in Humeida et al., "A Probabilistic Approach for the Optimisation of Ultrasonic Array Inspection Techniques," *NDT & E International*, Vol. 68, December 2014, pp. 43-52.

Although described primarily with reference to attachment features, the transmitters and receivers described herein may be coupled to any metallic structures capable of transmitting a signal without prohibitive signal loss, and which are coupled to a composite component. The structures allow inspection of the composite component without removing a thermal blanket. For example, the structures may penetrate through an insulation layer and couple the insulation layer to the composite component. The metallic structure may be a bumper or a bracket which is coupled to the composite structure. The bumper may help define a pathway to transmit loads from one component to another. Similarly, although described primarily as metallic structures, the attachment features may comprise any suitable material which may transmit a signal from a transmitting device to a receiving device. Any number of transmitting or receiving devices may be coupled to an array of attachment features which may allow for quick evaluation of large areas.

While the damage detection systems described herein have been described in the context of aircraft applications, one will appreciate in light of the present disclosure that the system described herein may be used in connection with various other vehicles, for example, a launch vehicle, a spacecraft, an unmanned aerial vehicle, a missile, cars, trucks, busses, trains, boats, and submersible vehicles, or any other vehicle or device, or in connection with industrial processes, or propulsion systems, or any other system or process having composite materials.

In the detailed description herein, references to "one embodiment", "an embodiment", "various embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described herein with regard to specific embodiments. Furthermore, the connecting lines shown in the various figures contained herein are intended to represent various functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the inventions. The scope of the inventions is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

We claim:

1. A system for detecting damage in a back skin of a composite component comprising:
   the composite component comprising a core positioned between a top sheet and the back skin, the core comprising a plurality of cells;
   a first attachment feature coupled to the back skin of the composite component the first attachment feature comprising a first post and a first cap;
   a second attachment feature coupled to the back skin of the composite component, the second attachment feature comprising a second post and a second cap;
   a thermal protection system coupled to the back skin of the composite component via the first attachment feature and the second attachment feature, wherein the first attachment feature and the second attachment feature extend through the thermal protection system;
   a transmitting device embedded in the first attachment feature cap and configured to transmit a signal through the first attachment feature, an entire length the back skin situated between the first attachment feature and the second attachment feature, and the second attachment feature to a receiving device embedded in the second attachment feature cap,
   wherein the first cap is removably coupled to the first post and the second cap is removably coupled to the second post in order to remove the thermal protection system and access the back skin.

2. The system of claim 1, wherein at least one of the transmitting device or the receiving device comprise a piezoelectric transducer.

3. The system of claim 1, wherein the receiving device is configured to receive a signal from the transmitting device.

4. The system of claim 1, wherein the composite component comprises a back skin for an acoustic structure.

5. The system of claim 1, wherein the first attachment feature and the second attachment feature are metallic.

6. A method of detecting damage in a back skin of a composite component comprising:
   embedding a transmitting device in a cap of a first attachment feature, wherein the first attachment feature cap is removably coupled to a first attachment feature post and wherein the first attachment feature is coupled to the back skin of the composite component, the composite component comprising a core positioned between a top sheet and the back skin, the core comprising a plurality of cells;
   embedding a receiving device in a cap of a second attachment feature, wherein the second attachment feature cap is removably coupled to a second attachment feature post and wherein the first attachment feature is coupled to the back skin of the composite component;
   wherein the first attachment feature and the second attachment feature couple a thermal protection system to the back skin of the composite component, wherein the first attachment feature and the second attachment feature extend through the thermal protection system, and wherein the first attachment feature cap is removably coupled to the first attachment feature post and the second attachment feature cap is removably coupled to the second attachment feature post in order to remove the thermal protection system and access the back skin;
   transmitting a signal from the transmitting device, through the first attachment feature, through an entire length of the back skin situated between the first attachment feature and the second attachment feature, and through the second attachment feature to the receiving device; and
   detecting, based on the signal, damage in the back skin of the composite component.

7. The method of claim 6, wherein the signal comprises an ultrasonic wave pattern.

8. The method of claim 6, further comprising receiving the signal at the receiving device.

9. The method of claim 8, further comprising comparing the signal received at the receiving device to an expected signal for an undamaged composite component.

10. The method of claim 6, wherein at least one of the transmitting device or the receiving device comprise a piezoelectric transducer.

11. The method of claim 6, wherein the composite component comprises an acoustic structure.

* * * * *